(12) United States Patent
Lee

(10) Patent No.: US 8,256,848 B2
(45) Date of Patent: Sep. 4, 2012

(54) METHOD FOR MAKING INTERDENTAL BRUSH

(75) Inventor: Chia-Fu Lee, Kaohsiung County (TW)

(73) Assignee: Lee Chia Brush Co., Ltd., Kaohsiung County (TW)

(*) Notice: Subject to any disclaimer, the term of this patent is extended or adjusted under 35 U.S.C. 154(b) by 424 days.

(21) Appl. No.: 12/686,652

(22) Filed: Jan. 13, 2010

(65) Prior Publication Data

US 2011/0169322 A1 Jul. 14, 2011

(51) Int. Cl.
*A46D 3/04* (2006.01)
(52) U.S. Cl. .......... 300/21; 300/4; 300/8; 15/167.1
(58) Field of Classification Search .......... 15/167.1, 15/320; 300/4, 8, 21; *A46D 3/04*
See application file for complete search history.

(56) References Cited

U.S. PATENT DOCUMENTS

2011/0314624 A1* 12/2011 Kubo .......... 15/167.1

* cited by examiner

*Primary Examiner* — Robert Scruggs
(74) *Attorney, Agent, or Firm* — Rosenberg, Klein & Lee

(57) ABSTRACT

The method for making an interdental brush inserts a bristle stem into a through hole of a handle in a combining step, whereby exposing the stem to each fixing slot on the handle. Thence the stem is further punched by a punching device, allowing a correspondent formation of expanding portions. Hereby, the expanding portions have an outermost diameter larger than an opening of the through hole for the stem to be firmly lodged in the fixing slots in a fixing step. A filler for wrapping the entire handle and the stem offers a solid engagement between the expanding portions and the fixing slots, so that the stem does not depart from the handle while using.

3 Claims, 9 Drawing Sheets

METHOD FOR MAKING INTERDENTAL BRUSH

BACKGROUND OF THE INVENTION

1. Field of the Invention

The present invention relates to a method, particularly to a method for making an interdental brush.

2. Description of the Related Art

FIG. 1 show "A Method for Making an Interdental Brush" issued by a Japan publication No. 10-155546. The conventional interdental brush 1 comprises a handle 11, a bristle stem 12 connected to the handle 11, and a filler 13 for wrapping the handle 11 up. Wherein, the handle 11 includes a handle body 111, a plurality of apertures 112 respectively defined on the handle body 111 at intervals, and a through hole 113 placed on one end of the handle body 111 and intercommunicated with the apertures 112. In manufacturing, one end of the bristle stem 12 is inserted into the through hole 113, and thence rods 14 are put in the apertures 112 for propelling the bristle stem 12 inside the through hole 113 so as to form a bent portion 121 with a bending angle α on the bristle stem 12. Finally, the filler 13 is able to fill the through hole 113 and the apertures 112, and the completion of the interdental brush 1 is achieved.

However, although the bristle stem 12 is propelled by the rods 14 to form bent portions thereon, the bent portions of the bristle stem 12 do not clasp any engaging portion. As a result, even if the bristle stem 12 is wrapped in the filler 13, a slight pulling force is able to pull the bristle stem 12 out, thus incurring an unstable engagement between the bristle stem 12 and the handle 11. Moreover, since the bristle stem 12 is twisted by wires, such formation readily brings on the resilience after the propelling. Namely, even if a certain bent portion is formed while the bristle stem 12 is thrust, the resilience generated therefrom still lessening the bending angle α of the bristle stem 12. Therefore, the engagement between the bristle stem 12 and the handle 11 is influenced and an improvement is needed.

In order to remove abovementioned shortcomings, another method for making an interdental brush issued by an EP patent application no. 1625808A1 is shown in FIG. 2. The interdental brush 2 comprises a handle 21, a bristle stem 22 connected to the handle 21, and a filler 23 for wrapping the handle 21 up. Wherein, the handle 21 includes a handle body 211, two fixing slots 212 defined on the handle body 211 at intervals and communicated with the exterior, a through hole 213 positioned on the handle body 211 and intercommunicated with the fixing slots 212, and a fixing hole 214 placed on the handle body 211 and correspondent with the fixing slots 212. In manufacturing, the bristle stem 22 is sequentially inserted into the through hole 213 until being fixed into the fixing hole 214. Thereafter, a rod 24 is employed to shove the bristle stem 22 in one of the fixing slots 212 for generating a bent portion 221 on the bristle stem 22, so that the bent portion 221 would be able to engage with the fixing slot 212. Lastly, the filler 23 is applied to wrap the fixing slot 212 up for achieving a finished interdental brush 2.

However, in using, even if the bent portion 221 is able to engage with the fixing slot 212 for increasing a firm combining effect between the bristle stem 22 and the handle 21, the resilience on the bristle stem 21 still exists after removing the shoving force from the rod 24. Namely, while taking away the shoving from the rod 24, the bending angle of the bent portion 221 is too slight to firmly engage with the fixing slot 212. As a result, the combining effect between the bristle stem 21 and the handle 21 is influenced and awaiting an improvement.

Another interdental brush issued by a JP patent application no. 2009-247531 is shown in FIG. 3. The interdental brush 3 comprises a handle 31, a bristle stem 32 connected to the handle 31, and a filler 33 for wrapping the handle 31 up. Wherein, the handle 31 includes a through hole 311 defined thereon and a plurality of fixing slots 312. Moreover, the fixing slots 312 are not intercommunicated with the through hole 311; namely, an encompassing portion 313 is formed around the exterior of the through hole 311. Thereby, after inserting the bristle stem 32 into the through hole 311, an extruding device is employed to extrude the encompassing portion 313 from the fixing slots 312 so as to correspondingly extrude and fix the bristle stem 32. Consequently, the fixing slots 312 would be wrapped in the filler 33 for achieving the finished interdental brush 3. However, in such extruding manner, the encompassing portion 313 adopts the plastic material that is characterized by a higher plasticity, and the bristle stem 32 adopts the metal material that possesses a lower malleability. Accordingly, when the encompassing portion 313 is extruded, the bristle stem 32 would not be efficiently deformed by the coming encompassing portion 313. Instead, the bristle stem 32 is subjected to sink in the encompassing portion 313. Further, since the fixing slots 312 are not intercommunicated with the through hole 311, the stem 32 is incapable of being wrapped well while the filler 33 is applied. Therefore, during the using, the bristle stem 32 readily departs from the handle 31 in view of any accidental external pulling and dragging. Thus, an improvement is still needed.

SUMMARY OF THE INVENTION

The object of the present invention is to provide a method for making an interdental brush, which could firmly and precisely fix the bristle stem for promoting the productivity and decreasing the manufacturing cost.

The method for making the interdental brush in accordance with the present invention comprises a preparing step, a combining step, a fixing step, and a forming step.

Characterized in that, a punching device is provided in the fixing step for punching a bristle stem with a portion that is exposed to every fixing slot so as to form a plurality of expanding portions on the bristle stem. Moreover, an outermost diameter of the expanding portions is larger than an opening of a through hole, so that the bristle stem is able to firmly engage within the fixing slots. In the forming step, a filler wraps the bristle stem and a handle for further providing a solid combination, so that the bristle stem would not depart from the handle in time of using.

An object of the instant invention is to provide a method for making an interdental brush sequentially comprising a preparing step for setting a bristle stem with twisted bristles and a handle with spaced fixing slots that communicates with the exterior as well as a through hole inside the handle, in which a fixing hold is placed to correspond to the through hole; a combining step for inserting the bristle stem into the fixing hole and exposing the bristles out of the handle; a fixing step for punching a portion of the bristle stem exposed to every fixing slot so as to form correspondent expanding portions having an outermost diameter lager than an opening of the through hole, by which said bristle stem could be firmly engaged and embedded in the fixing slots; and a forming step for forming a filler applied to wrap the fixing slots up so as to fixedly envelope the bristle stem and the expanding portions to form an integral interdental brush.

Preferably, the through hole is formed by a taper, and an opening of the through hole that is closed to the fixing slot is smaller than an opening of the through hole that is communicated with the exterior.

Preferably, a mark area is formed on the handle after the filler wrapping the fixing slots up for presenting marks.

The advantages of the present invention over the known prior arts will become more apparent to those of ordinary skilled in the art upon reading the following descriptions in junction with the accompanying drawings.

DETAILED DESCRIPTION OF THE PREFERRED EMBODIMENTS

Figure 1:
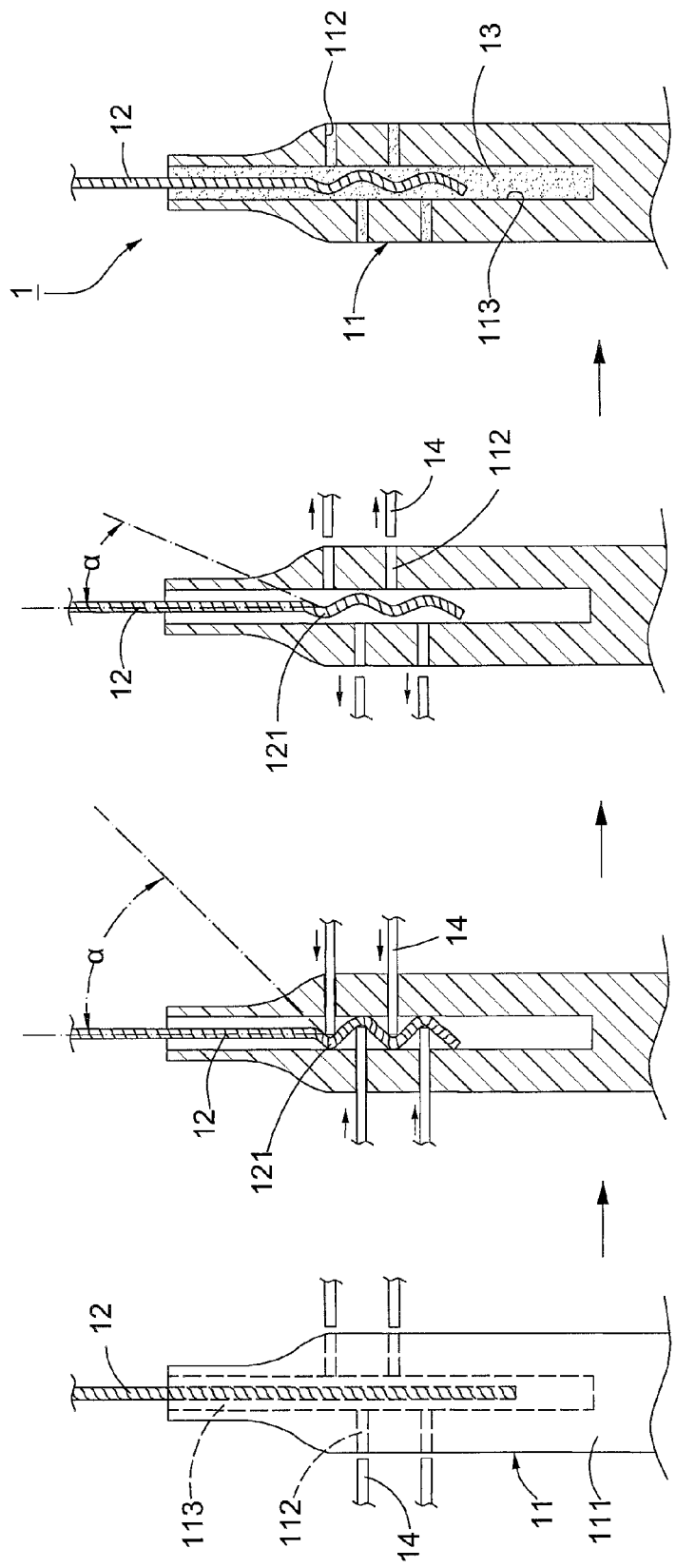
FIG. 1 is a schematic view showing procedures of a conventional method for making the interdental brush.
Figure 2:
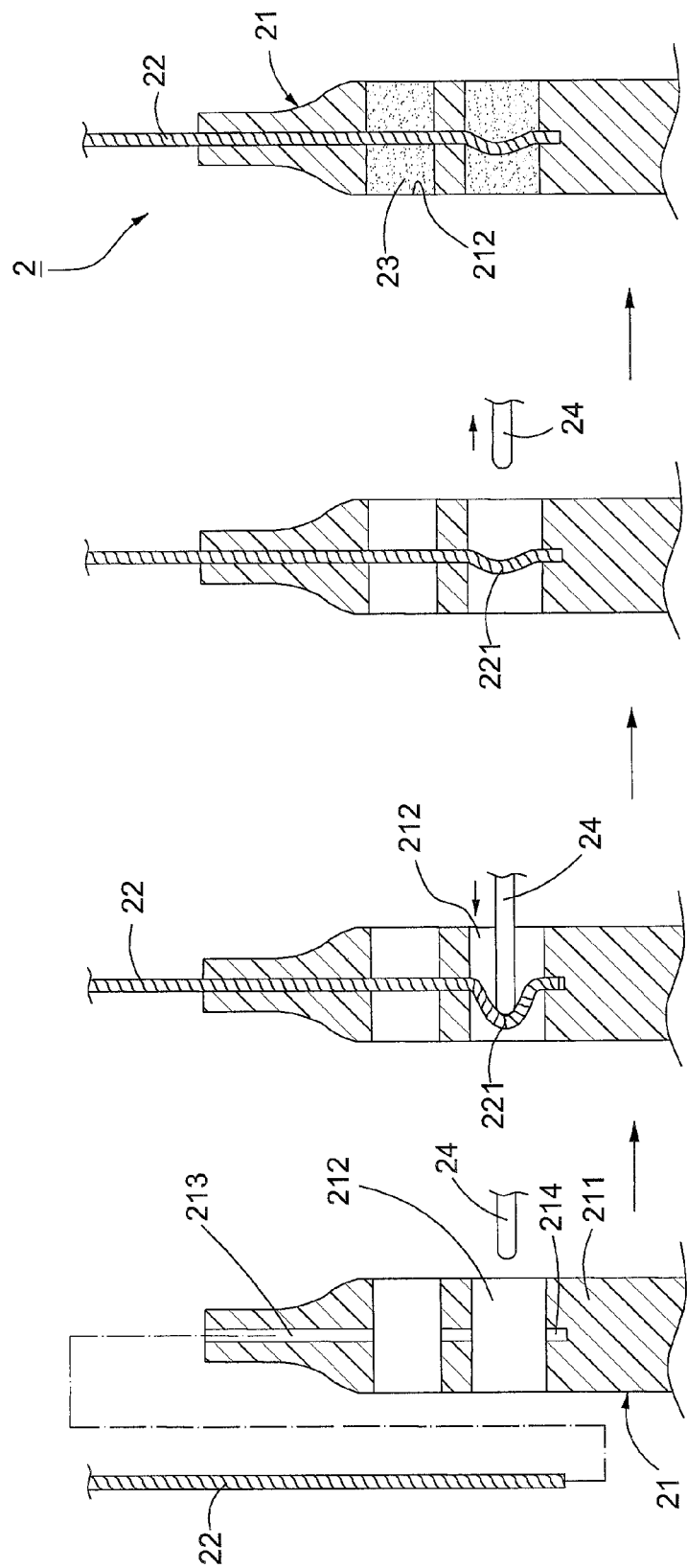
FIG. 2 is a schematic view showing procedures of another conventional method for making the interdental brush.
Figure 3:
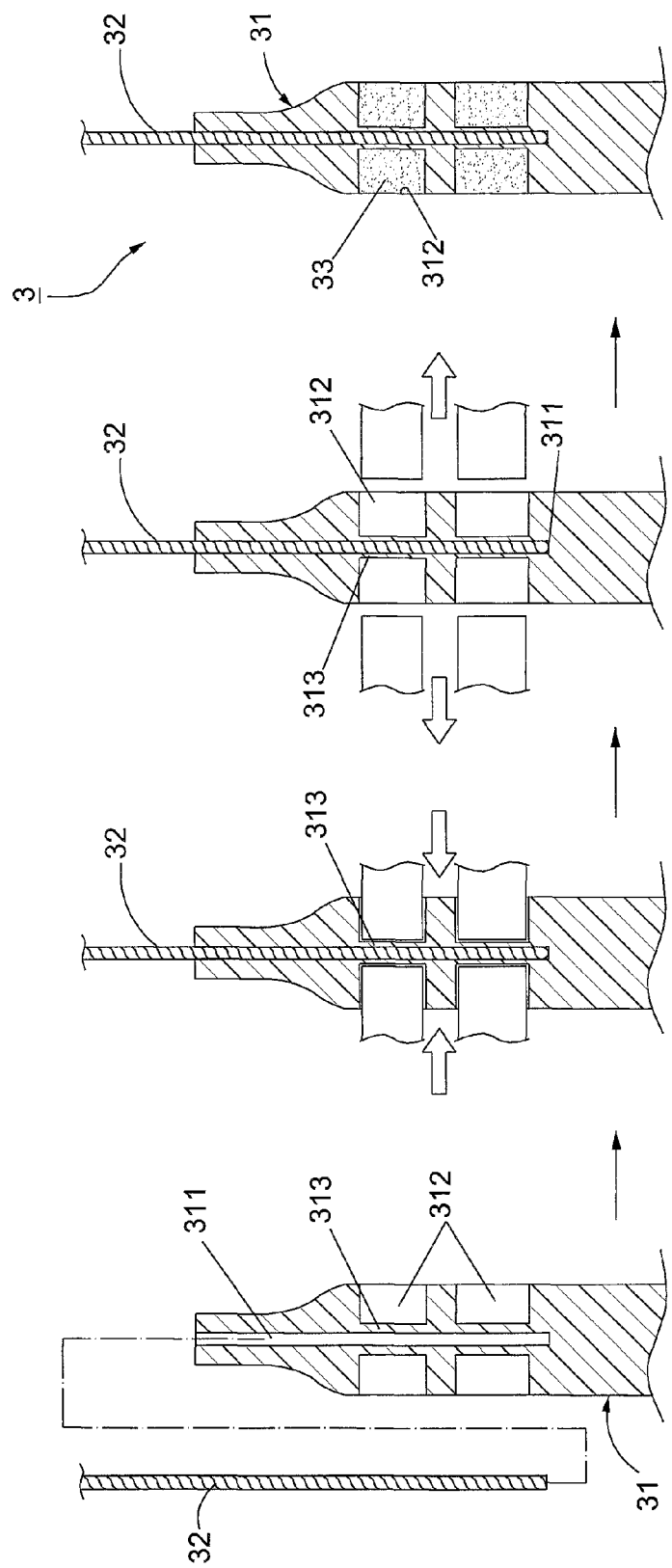
FIG. 3 is a schematic view showing procedures of another conventional method for making the interdental brush.
Figure 4:
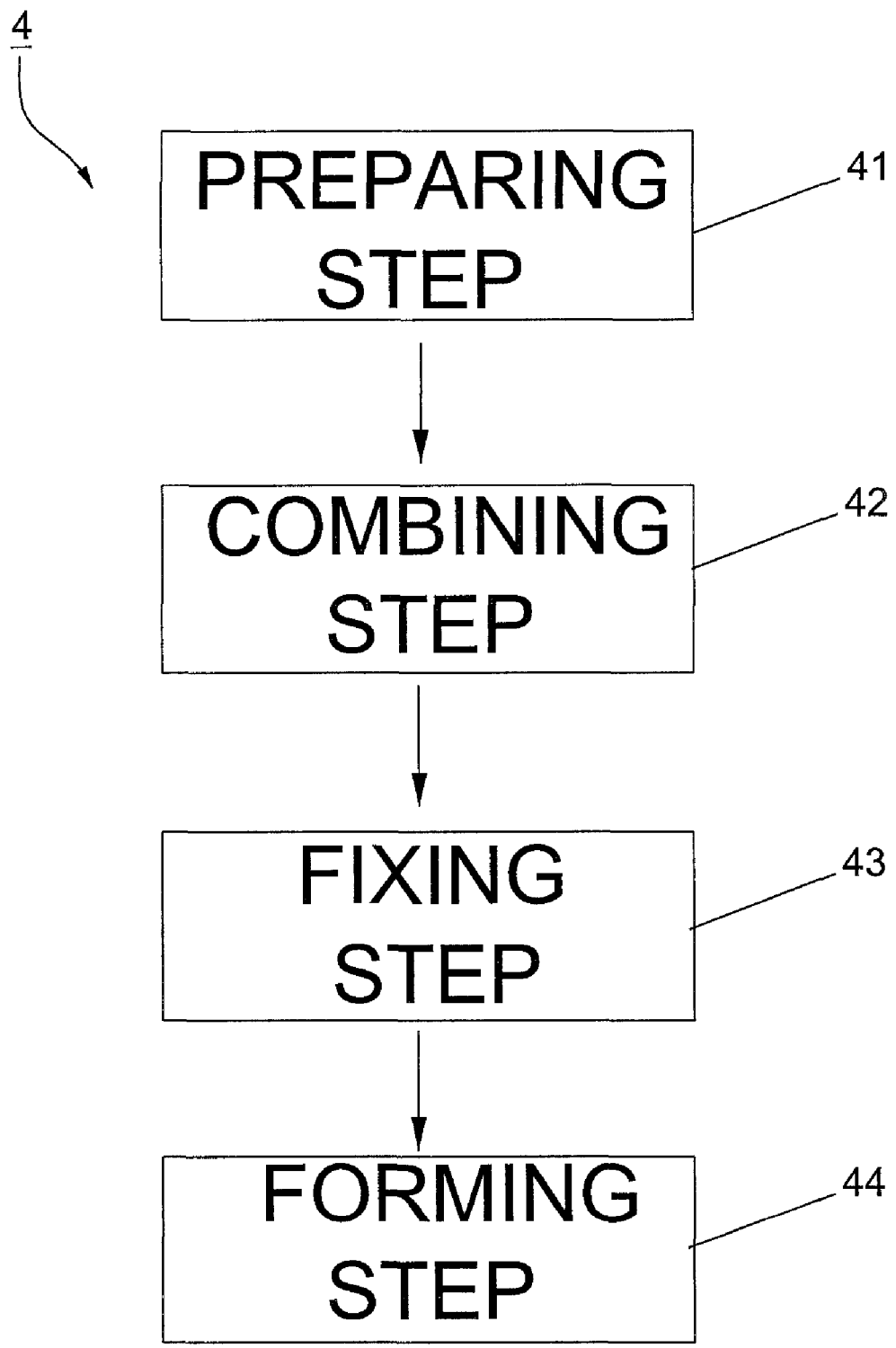
FIG. 4 is a flowchart showing a first preferred embodiment of the present invention.
Figure 5:
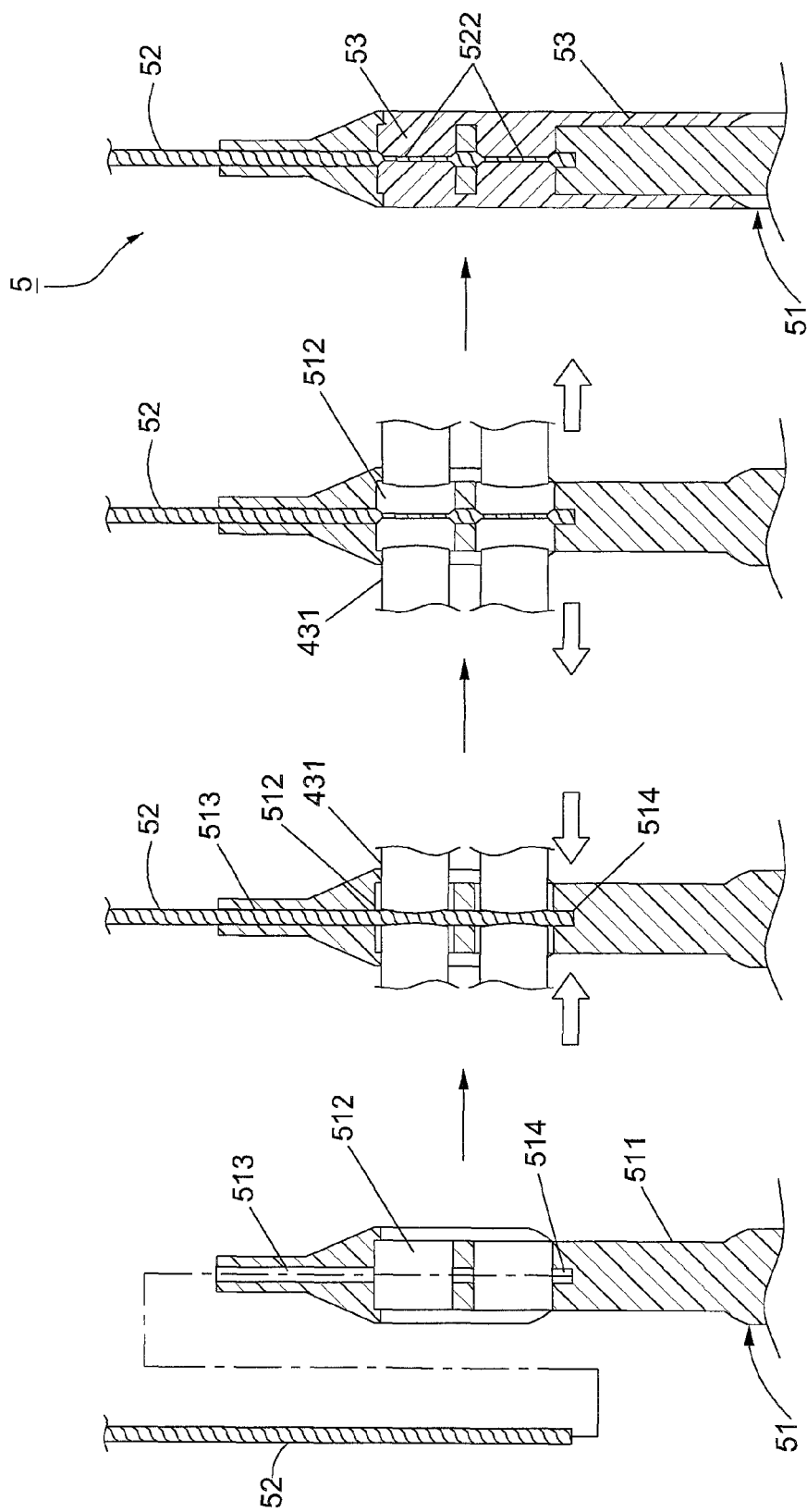
FIG. 5 is schematic view showing forming procedures of the first preferred embodiment of the present invention.
Figure 6:
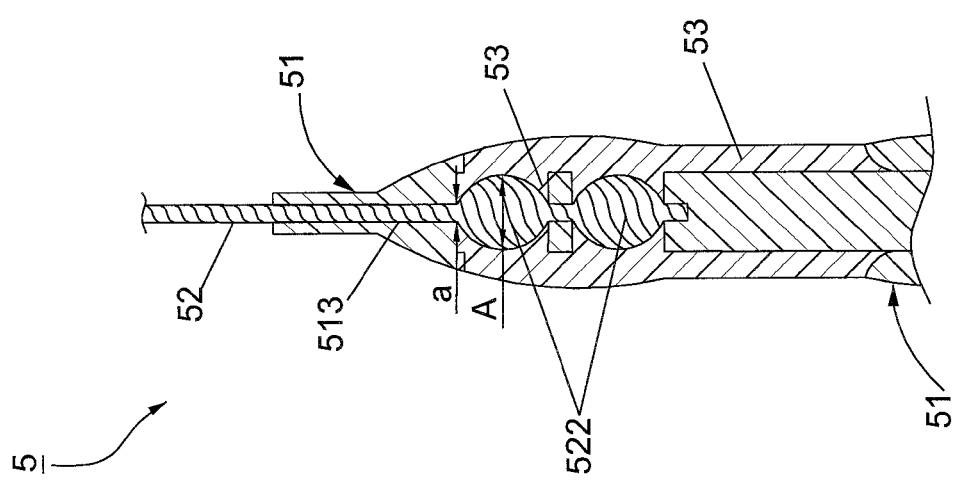
FIG. 6 is a front view showing the final product of FIG. 5.

FIGS. 4 to 6 show a first preferred embodiment of the present invention, a method 4 allowable for manufacturing an interdental brush sequentially comprising a preparing step 41, a combining step 42, a fixing step 43, and a forming step 44. Wherein, in the preparing step 41, a handle 51 and a bristle stem 52 are provided. Moreover, the handle 51 includes a handle body 511, a plurality of fixing slots 512 respectively defined on the handle body 511 at intervals and communicated with the exterior, a through hole 513 positioned on the handle body 511 and intercommunicated with the fixing slots 512, and a fixing hole 514 placed on the handle body 511 for corresponding with the through hole 513. Further, a plurality of bristles 521 is twisted on the bristle stem 52, and a mark area 515 (as shown in FIGS. 7 and 8) is additionally provided on the handle 51 for showing trademarks or other patterns.

Continuing with the aforesaid, in the combining step 42, the other end of the bristle stem 52 passes through the through hole 513 on the handle body 511 until being fixed in the fixing hole 514. In addition, in the fixing step 43, a punching device (not shown) includes dies 431 (shown by a sketch) for correspondingly forming the fixing slots 512. Thereby, by using the dies 431 to punch on the bristle stem 52 having the portion exposed to the fixing slots 512, a plurality of flat expanding portions 522 are consequently formed. Herein, an outermost diameter A of the expanding portions 522 is defined larger than an opening a of the through hole 513, so that the expanding portions 522 of the bristle stem 52 are able to firmly engage within the fixing slots 512 as shown in FIG. 6.

Figure 7:
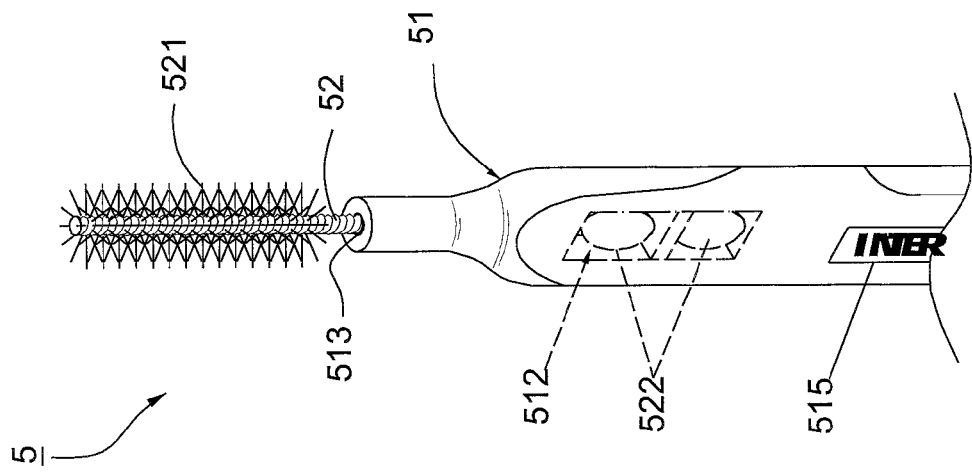
FIG. 7 is perspective view showing the first preferred embodiment of the present invention.
Figure 8:
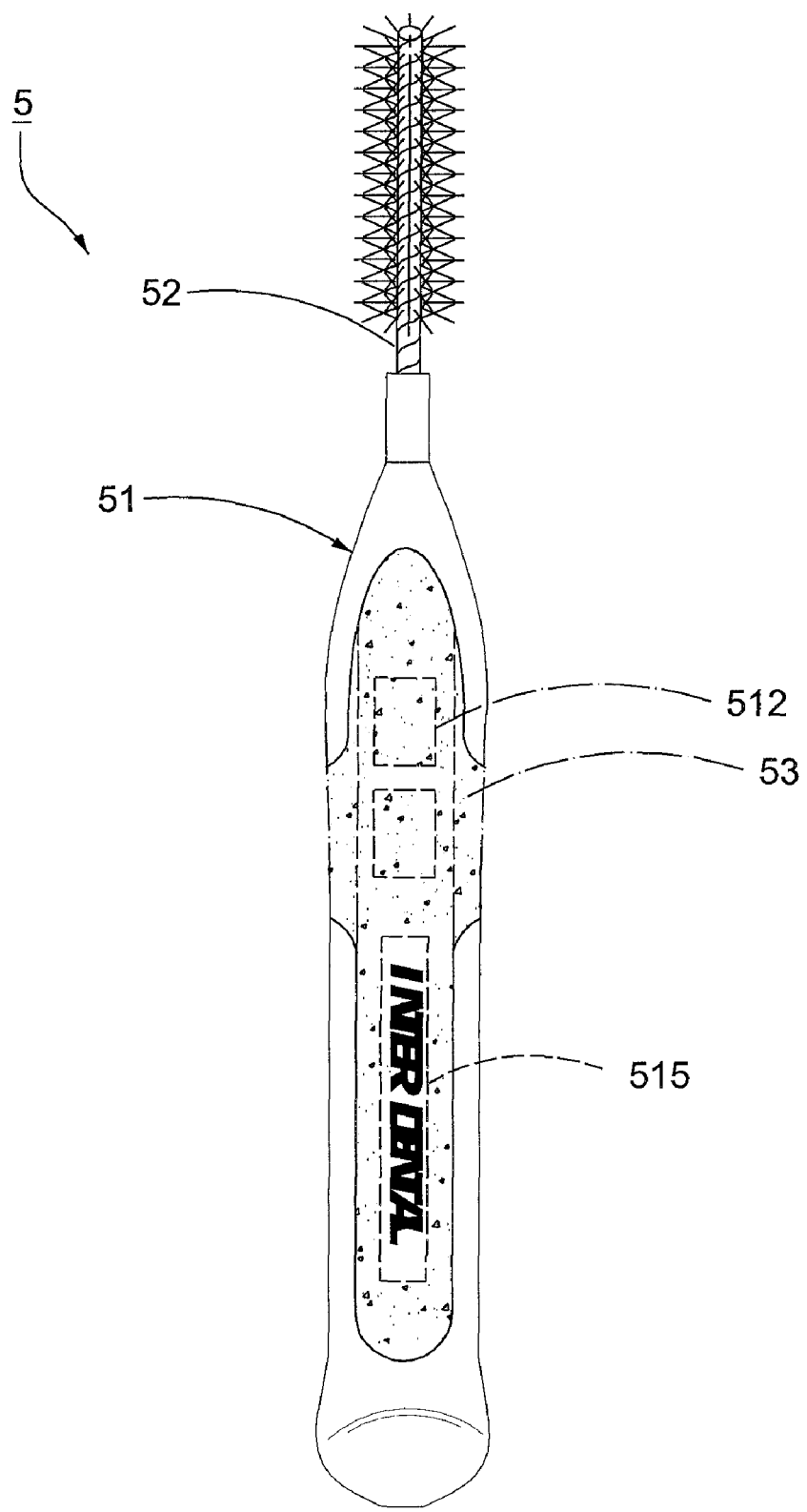
FIG. 8 is a front view showing the first preferred embodiment of the present invention.

Accompanying with FIGS. 7 and 8, finally in the forming step 44, an injection molding machine (not shown) is provided for forming a filler 53, which fills up the fixing slots 512 and envelops the bristle stem 52. Accordingly, the bristle stem 52 in the fixing slots 512 would be firmly combined with the handle 51. That is, the flat expanding portions 522 on the bristle stem 52 are tightly wedged in the through hole 513, the fixing hole 514, and the filler 53, so a solid construction is achieved for preventing the escape or the unstable engagement between the bristle stem 52 and the handle 51. Preferably, since the mark area 515 is adopted in this embodiment, the filler 53 would favorably promote the presentation of the mark area 515 on the handle 51, rather than adversely cover the mark area 515. Thus, a finished interdental brush 5 is achieved.

Subsequently, by the cooperation of the through hole 513 and the fixing hole 514 of the handle 51, the places on the bristle stem 52 which are exposed to the fixing slots 512 are able to be directly punched by the punching device for forming the expanding portions 522 in the fixing step 43. Additionally, the outermost diameter A of every expanding portions 522 is set larger than an opening a of the through hole 513, thence permitting the bristle stem 52 to be firmly lodged in the fixing slots 512 via the engagement between the expanding portions 522 and the through hole 513. As a result, the filler 53 would be employed to fill up the fixing slots 512 in the forming step 44, so that the bristle stem 52 would be also wrapped therein for firmly combining with the fixing slots 512 and the handle 51. Therefore, the bristle stem 52 avoids the disadvantage of readily departing from the handle 51.

Figure 9:
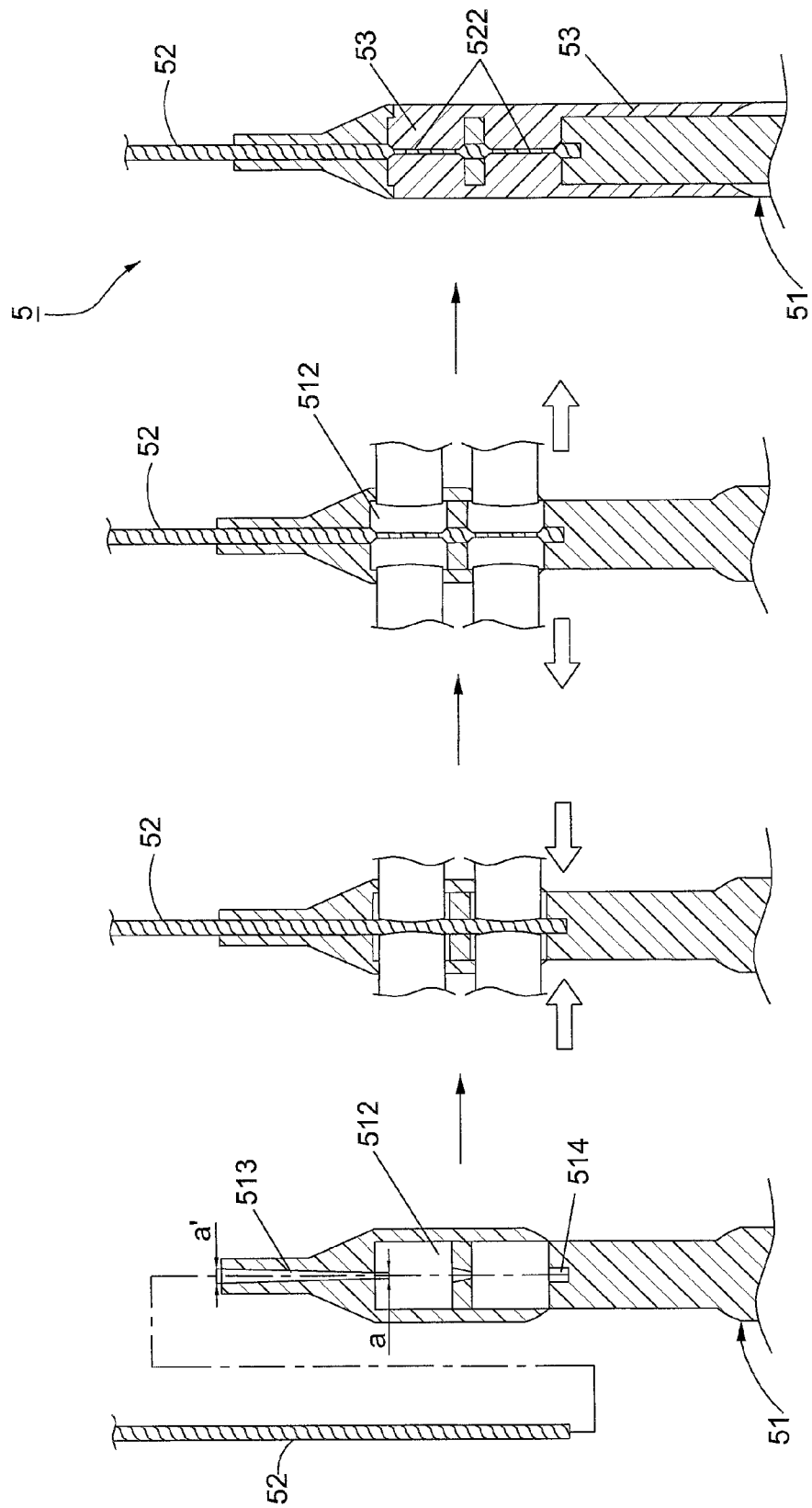
FIG. 9 is a schematic view showing forming procedures of a second preferred embodiment of the present invention.
Figure 10:
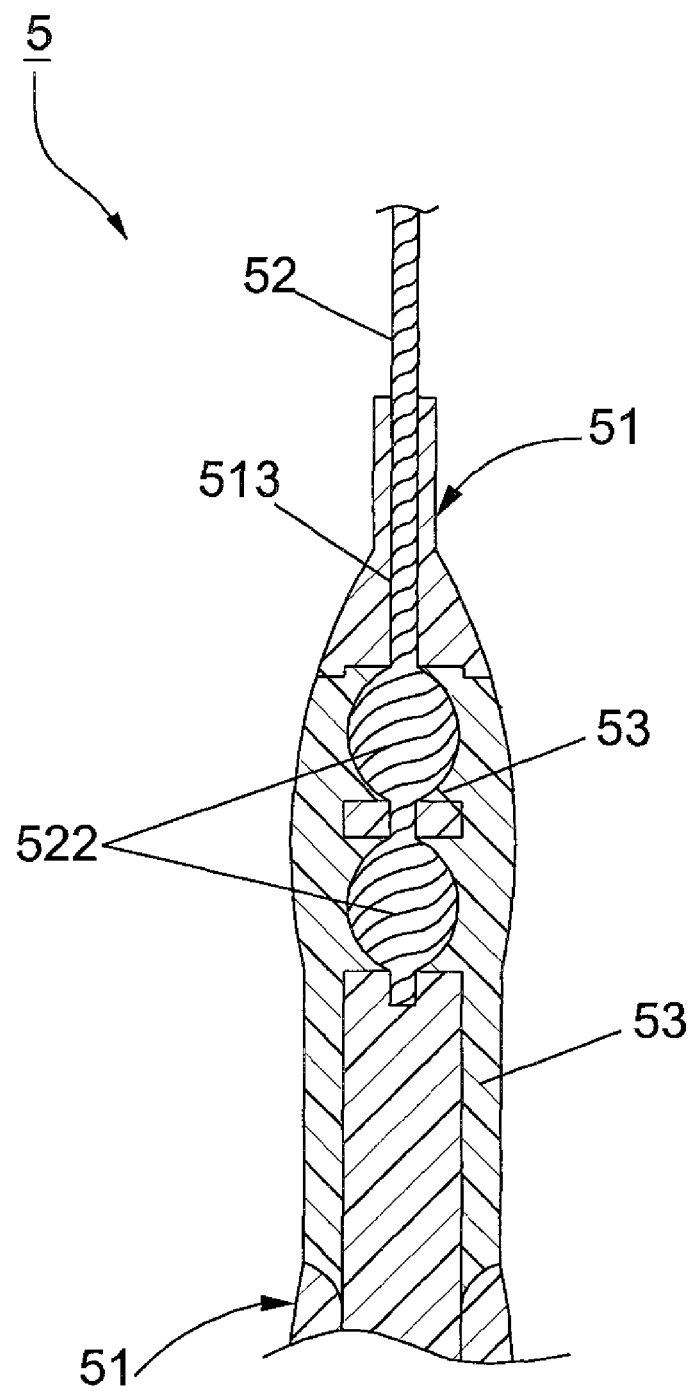
FIG. 10 is a side view of the final product of FIG. 9.

Referring to FIGS. 9 and 10, a second preferred embodiment is shown. The discrepancy in the two embodiments is that one end of the through hole 513 is formed by a taper, and an opening a of the through hole 513 closed to the fixing slot 512 is defined smaller than an opening a' of the through hole communicated with the exterior. Namely, when the bristle stem 52 passes the opening a' through the opening a for being fixed in the fixing slots 512, the tapered opening a would tightly compress the bristle stem 52, allows which to be firmly lodged in the through hole 513 and the fixing hole 514. Afterward, while applying the punching on the bristle stem 52 to form the expanding portions 522 in the next step, the expanding portions 522 would be positioned within the fixing slots 512 and concurrently blocked by the opening a. By means of the wrapping from the filler 53, the fixing slots 512 and the handle 51 would be more tightly combined for preventing the bristle stem 52 to come off the handle 51 due to any unintentional pulling and dragging force. Thus, a rigid combination between the bristle stem 52 and the handle 51 is achieved.

To sum up, the present invention takes advantage of the expanding portions on the bristle stem being punched in the fixing step to offer a solid engagement with the fixing slots. Further, a filler applied in the forming step justly wraps the bristle stem up, which increases the firmness of the entire structure. Thus, the bristle stem would not readily come off the handle in time of using.

While we have shown and described the embodiment in accordance with the present invention, it should be clear to those skilled in the art that further embodiments may be made without departing from the scope of the present invention.

What is claimed is:

1. A method for making an interdental brush sequentially comprising preparing a handle and a bristle stem with a plurality of bristles twisted thereon; wherein, said handle having a handle body, a plurality of fixing slots defined on said handle body at intervals and communicated with the exterior, a through hole positioned on said handle body and intercommunicated with said fixing slot, and a fixing hole placed on said handle body and set correspondently to said through hole;

inserting said bristle stem being into said through hole and fixed in said fixing hole for a combination, allowing an exposure of said bristle out of said handle;

fixing said bristle stem in said handle body by preparing a punching device to punch said bristle stem with a portion thereof that is exposed to said fixing slots, thence allowing a plurality of expanding portions to be correspondingly formed on said bristle stem; wherein, said expanding portions having an outermost diameter lager than an opening of said through hole, permitting said bristle stem to be firmly engaged and embedded in said fixing slot; and forming an integral interdental brush by applying an injection molding machine to form a filler, which appropriately wraps said fixing slots up for fixedly enveloping said bristle stem and said expanding portions.

2. The method as claimed in claim 1, wherein said through hole is formed by a taper, and an opening of said through hole that is closed to said fixing slot is smaller than an opening of said through hole that is communicated with the exterior.

3. The method as claimed in claim 1, wherein, a mark area is formed on said handle after said filler wrapping said fixing slots up for presenting marks.

* * * * *